(12) United States Patent
Rocco

(10) Patent No.: US 6,376,505 B1
(45) Date of Patent: Apr. 23, 2002

US006376505B1

(54) 5-HT$_{1A}$ AND 5-HT$_{1D\alpha}$ ALPHA ANTAGONISTS

(75) Inventor: Vincent P. Rocco, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/423,348

(22) PCT Filed: May 11, 1998

(86) PCT No.: PCT/US98/09562

§ 371 Date: Nov. 22, 1999

§ 102(e) Date: Nov. 22, 1999

(87) PCT Pub. No.: WO98/53823

PCT Pub. Date: Dec. 3, 1998

Related U.S. Application Data

(60) Provisional application No. 60/048,256, filed on May 29, 1997.

(51) Int. Cl.$^7$ .................... A61K 31/438; C07D 471/10

(52) U.S. Cl. ........................................ 514/278; 546/17
(58) Field of Search .............................. 546/17; 514/278

(56) References Cited

U.S. PATENT DOCUMENTS

| | | | |
|---|---|---|---|
| 4,031,224 A | 6/1977 | Martin et al. | 514/278 |
| 5,420,150 A | 5/1995 | Guillaumet et al. | 514/409 |

FOREIGN PATENT DOCUMENTS

| | | | |
|---|---|---|---|
| EP | 0 518 805 A | 12/1992 | C07D/221/20 |
| EP | 0 722 941 A2 | 7/1996 | C07D/401/12 |

OTHER PUBLICATIONS

Moltzen E. K., et al., *J. Med. Chem.*, 38:11, pp. 2009–2017 (1995).

*Primary Examiner*—Alan L. Rotman
(74) *Attorney, Agent, or Firm*—Charles T. Joyner; Nelson L. Lentz

(57) ABSTRACT

A class of novel substituted-aryloxy-2-ol-3-(4-spiro-(alkanedioxy)isobenzofuranyl- and phthaloyl-piperidine) derivatives is disclosed useful as 5-HT$_{1A}$ and 5-HT$_{1D\alpha}$ antagonists.

21 Claims, No Drawings

5-HT$_{1A}$ AND 5-HT$_{1D\alpha}$ALPHA ANTAGONISTS

This application is a 371 of PCT/US98/09562, filed May 11, 1998, and claims benefit of provisional applications No. 60/048,256, filed May 29, 1997.

The present invention belongs to the fields of pharmacology and medicinal chemistry, and provides new pharmaceuticals which are useful for the treatment of diseases which are caused or affected by disorders of the serotonin-affected neurological systems, particularly those relating to the serotonin $1_A$ and $1_{D\alpha}$ receptors.

Pharmaceutical researchers have discovered in recent years that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generation of serotonin-affecting drugs tended to have a variety of different physiological functions, considered from both the mechanistic and therapeutic points of view. For example, many of the tricyclic antidepressant drugs are now known to be active as inhibitors of serotonin reuptake, and also to have anticholinergic, antihistamine or anti-alpha-adrenergic activity. More recently, it has become possible to study the function of drugs at individual receptors in vitro or ex vivo, and it has also been realized that therapeutic agents free of extraneous mechanisms of action are advantageous to the patient. Accordingly, the objective of research now is to discover agents which affect only functions of serotonin, for example, at specific identifiable receptors.

Over the last several years it has become apparent that serotonin is associated directly or indirectly with a number of physiological phenomena, including appetite, memory, thermo-regulation, sleep, sexual behavior, anxiety, depression, and hallucinogenic behavior [Glennon, R. A., *J. Med. Chem.* 30, 1 (1987)].

5-HT receptors have been identified in the central nervous system (CNS; brain and spinal cord) and in peripheral tissues including the gastrointestinal tract, lung, heart, blood vessels, and various other smooth muscle tissues.

It has been recognized that there are multiple types of 5-HT receptors. These receptors have been classified as 5-HT$_1$, 5-HT$_2$ and 5-HT$_3$ receptors, with the former being further divided into the sub-classes 5-HT$_{1A}$, 5-HT$_{1B}$, 5-HT$_{1C}$, 5-HT$_{1D}$, 5-HT$_{1E}$ and 5-HT$_{1F}$.

Few ligands have selectivity for 5-HT$_{1D}$ receptors. Sumatriptan possesses limited 5-HT$_{1D}$ selectivity. GR 127935 has also been identified as a potent and selective 5-HT$_{1D}$ receptor antagonist. Hayer, et al., *Pharmacological Reviews*, Vol. 46, No. 2, pp. 157–203 (1994).

Molecular cloning has demonstrated that pharmacologically defined 5-HT$_{1D}$ receptors are encoded by two separate but closely related genes, designated 5-HT$_{1D\alpha}$ and 5-HT$_{1D\beta}$, which are members of the GPRC superfamily. These receptors display highly conserved transmembrane homology (75%) and similar binding properties and second messenger coupling (inhibition of adenylate cyclase). Leonhardt, S., et al., *J. Neurochem*, 53:465–471 (1989).

It is desirable to develop new compounds and treatments for 5-HT$_{1A}$ and 5-HT$_{1D\alpha}$ receptor mediated diseases.

We have now discovered a class of compounds which have activity both at the 5-HT$_{1A}$ and 5-HT$_{1D\alpha}$ receptor.

This invention provides a compound of formula I

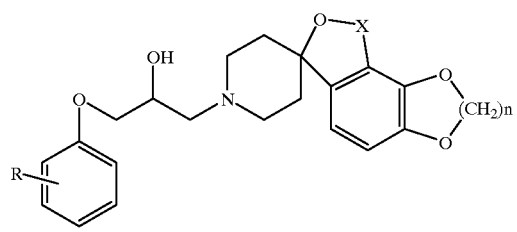

wherein:

R is —(C$_3$–C$_{10}$)cycloalkyl or —S(C$_1$–C$_{10}$)alkyl;

X is

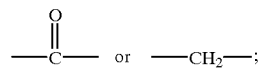

and n is an integer from 1 to 3 both inclusive;

or a pharmaceutically acceptable salt, racemate, optical isomer or solvate thereof.

This invention also provides a pharmaceutical formulation comprising a compound of formula I in association with one or more pharmaceutically acceptable diluents, carriers and excipients.

This invention further provides a method of inhibiting the 5-HT$_{1A}$ receptor comprising administering to a mammal in need of such treatment a therapeutically effective amount of a direct acting 5-HT$_{1A}$ antagonist of formula I.

This invention provides in addition a method of inhibiting the 5-HT$_{1D\alpha}$ receptor comprising administering to a mammal in need of such treatment a therapeutically effective amount of a direct acting 5-HT$_{1D\alpha}$ antagonist of formula I.

This invention further provides a method of inhibiting the 5-HT$_{1A}$ and 5-HT$_{1D\alpha}$ receptors comprising administering to a mammal in need of such treatment a therapeutically effective amount of a direct acting 5-HT$_{1A}$ and 5-HT$_{1D}$ antagonist of formula I.

This invention also provides a method of alleviating the pathological effects of diseases mediated by inhibiting the 5-HT$_{1A}$ receptor which comprises administering to a mammal in need of such treatment a therapeutically effective amount of a direct acting 5-HT$_{1A}$ antagonist of formula I.

Still further, this invention also provides a method of alleviating the pathological effects of diseases mediated by inhibiting the 5-HT$_{1D\alpha}$ receptor which comprises administering to a mammal in need of such treatment a therapeutically effective amount of a direct acting 5-HT$_{1D\alpha}$ antagonist of formula I.

This invention also provides a method of alleviating the pathological effects of diseases mediated by inhibiting the 5-HT$_{1A}$ and 5-HT$_{1D\alpha}$ receptors which comprises administering to a mammal in need of such treatment a therapeutically effective amount of a direct acting 5-HT$_{1A}$ and 5-HT$_{1D\alpha}$ antagonist of formula I.

Another aspect of the invention is a method of treating a mammal suffering from or susceptible to any condition mediated by inhibiting the 5HT$_{1A}$ receptor of the type represented by withdrawal or partial withdrawal from the use of tobacco or of nicotine; a method of alleviating the symptoms caused by withdrawal or partial withdrawal from the use of tobacco or of nicotine, a method of treating anxiety; and a method of treating a condition chosen from the group consisting of depression, hypertension, cognitive disorders, psychosis, sleep disorders, gastric motility disorders and obesity, substance abuse, obsessive-compulsive disease, panic disorder and migraine; which methods comprise administering to a subject in need of such treatment an effective amount of a compound of Formula I.

A still further aspect of the invention is a method of treating a mammal suffering from or susceptible to any condition mediated by inhibiting the $5HT_{1D\alpha}$ receptor of the type represented by depression, dementia, Parkinson's disease, anxiety, appetite modulation, sexual dysfunction, seasonal affective disorder, hyperprolactinemia, cerebral vascular disease, antisocial behavior, obsessive/compulsive disorder, amnesia, tardive dyskensia, hypertension and gastric motility disorder.

Other objects, features and advantages of the present invention will become apparent from the subsequent description and the appended claims.

Definitions

As used herein, the term, "$(C_1-C_{10})$alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, isopentyl, neopentyl, heptyl, hexyl, octyl, nonyl, decyl and the like. The term "$(C_1-C_{10})$alkyl" encompasses "$(C_1-C_6)$alkyl" and "$(C_1-C_4)$alkyl".

The term "$(C_3-C_{10})$ cycloalkyl" refers to a hydrocarbon ring having the stated number of carbon atoms. Typical $(C_3-C_{10})$ cycloalkyl groups include cyclopropyl, cyclobutyl, cyclopentyl, cyclohexyl, cycloheptyl, cyclooctyl, cyclononyl and cyclodecyl. The term "$(C_3-C_{10})$ cycloalkyl" includes "$(C_4-C_6)$ cycloalkyl".

The term "protecting group" is used herein as it is frequently used in synthetic organic chemistry, to refer to a group which will prevent a functional group from participating in a reaction carried out on some other functional group of the molecule, but which can be removed when it is desired to do so. Such groups are discussed by T. W. Greene in chapter 5 and 7 of *Protective Groups in Organic Synthesis,* John Wiley and Sons, New York, 1981, and by J. W. Barton in chapter 2 of *Protective Groups in Organic Chemistry,* J. F. W. McOmie, e., Plenum Press, New York, 1973, which are incorporated herein by reference in their entirety.

Nitrogen protecting groups refer to a group which will prevent an amino group from participating in a reaction. Examples of amino protecting groups include benzyl and substituted benzyl such as 3,4-dimethoxybenzyl, o-nitrobenzyl, and triphenylmethyl; those of the formula —COOR[1] where R[1] includes such groups as methyl, ethyl, propyl, isopropyl, 2,2,2-trichloroethyl, 1-methyl-1-phenylethyl, isobutyl, t-butyl, t-amyl, vinyl, allyl, phenyl, benzyl, p-nitrobenzyl, o-nitrobenzyl, and 2,4-dichlorobenzyl; acyl groups and substituted acyl such as formyl, acetyl, chloroacetyl, dichloroacetyl, trichloroacetyl, trifluoroacetyl, benzoyl, and p-methoxybenzoyl; and other groups such as methanesulfonyl, p-toluenesulfonyl, p-bromobenzenesulfonyl, p-nitrophenylethyl, and p-toluenesulfonyl-aminocarbonyl. Preferred amino-protecting groups are tert-butoxy or benzyl.

Useful compounds for practicing the method of the present invention includes pharmaceutically acceptable acid addition salts of the compounds defined by the above formula I. Acids commonly employed to form such salts are inorganic acids, such as hydrocholoric acid, hydrobromic acid, hydroiodic acid, sulfuric acid, phosphoric acid, and the like, and organic acids, such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts thus are the sulfate, pyrosulfate, bisulfate, sulfite, bisulfite, phosphate, monohydrogenphosphate, dihydrogenphosphate, metaphosphate, chloride, bromide, iodide, acetate, propionate, decanoate, caprylate, acrylate, formate, isobutyrate, caproate, heptancate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid, hydrobromic acid and organic acids such as acetic acid, oxalic acid, maleic acid or fumaric acid The compounds of the instant invention have one stereocenter at the carbon atom to which the hydroxy is attached and may be isolated in optically active and racemic forms. The optically active isomers of the racemates of invention are also considered within the scope of Formula I. Such optically active isomers may be prepared from their respective optically active precursors following the procedure described below, or by resolving the racemic mixtures. These resolutions can typically be carried out in the presence of a resolving agent, by chromatography or by repeated crystallization.

Procedures for separating racemates into their individual isomers can be found in references such as Jacques, et al., *Enantiomers, Racemates and Resolutions,* (John Wiley and Sons, New York 1981).

Preferred substituent groups of compounds of formula (I) include compounds where R is —$(C_4-C_6)$cycloalkyl or —$S(C_1-C_4)$alkyl and n is 2 or 3.

Of this preferred genus, compounds where R is cyclopentyl are more preferred.

The most preferred compounds of the instant invention are (2S)-(–)-1-(2-methylthiophenoxy)-3-(4,5-ethylenedioxy)spiro(isobenzofuran-1(3H),4'-piperidin)1'-yl)-2-propanol ethanedioate; (2S)-(–)-1-(2-methylthiophenoxy)-3-(4,5-ethylenedioxy)spiro (isobenzofuran-1(3H),4'-piperidin)-3-one-1'-yl)-2-propanol ethanedioate; (2S)-(–)-1-(2-cyclopentylphenoxy)-3-(4,5-ethylenedioxy)spiro(isobenzofuran-1(3H),4'-piperidin)-1'-yl)-2-propanol ethanedioate; (2S)-(–)-1-(2-cyclopentylphenoxy)-3-(4,5-ethyeneldioxy)spiro (isobenzofuran-1(3H),4'-piperidin)-3-one-1'-yl)-2-propanol ethanedioate and (2S)-(–)-1-(2-cyclopentylphenoxy)-3-(4, 5-propylenedioxy)spiro(isobenzofuran-1(3H),4'-piperidin)-3-one-1'-yl)-2-propanol ethanedioate.

Of these compounds, (2S)-(–)-1-(2-cyclopentylphenoxy)-3-(4,5-propylenedioxy)spiro(isobenzofuran-1(3H),4'-piperidin)-3-one-1'-yl)-2-propanol ethanedioate is particularly preferred.

Further typical examples of compounds of formula I which are useful in the present invention include:
2S)-(–)-1-(2-pentylthiophenoxy)-3-(4,5-ethylenedioxy) spiro(isobenzofuran-1(3H),4'-piperidin)1'-yl)-2-propanol maleate;

2S)-(−)-1-(2-ethylthiophenoxy)-3-(4,5-ethylenedioxy)spiro (isobenzofuran-1(3H),4'-piperidin)1'-yl)-2-propanol hydrochloride;

2S)-(−)-1-(2-propylthiophenoxy)-3-(4,5-methylenedioxy) spiro(isobenzofuran-1(3H),4'-piperidin)1'-yl)-2-propanol;

2S)-(−)-1-(2-cyclohexylphenoxy)-3-(4,5-propylenedioxy) spiro(isobenzofuran-1(3H),4'-piperidin-3-one-1'-yl)-2-propanol;

2S)-(−)-1-(2-cyclopropylphenoxy)-3-(4,5-ethylenedioxy) spiro(isobenzofuran-1(3H),4'-piperidin-3-one-1'-yl)-2-propanol maleate;

2S)-(−)-1-(2-cyclononylphenoxy)-3-(4,5-methylenedioxy) spiro(isobenzofuran-1(3H),4'-piperidin)1'-yl)-2-propanol ethanedioate;

2S)-(−)-1-(2-octylthiophenoxy)-3-(4,5-propylenedioxy) spiro(isobenzofuran-1(3H),4'-piperidin-3-one-1'-yl)-2-propanol ethanedioate; and 2S)-(−)-1-(2-methylthiophenoxy)-3-(4,5-methylenedioxy) spiro(isobenzofuran-1(3H),4'-piperidin)1'-yl)-2-propanol.

Synthesis Methods

Compounds of the instant invention can be prepared as described in Scheme I, below.

Scheme I

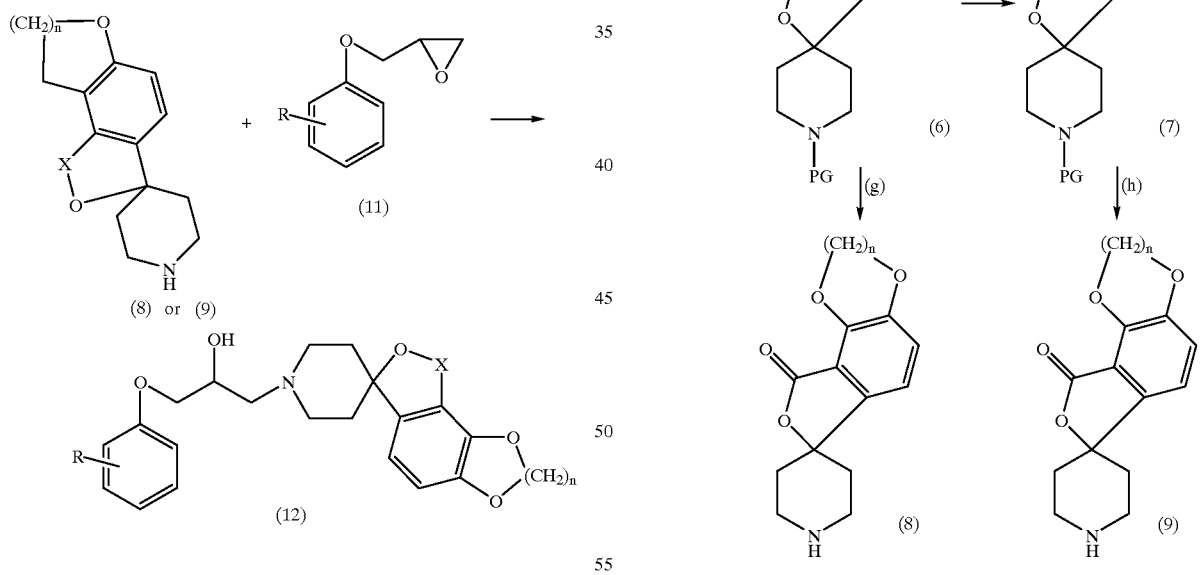

Desired product (12) is prepared by reacting (8) or (9) (prepared as described in scheme II below) with (11) (prepared as described in scheme III below) in acetonitrile or a lower alcohol solvent such as methanol for from about 1 to 24 hours. The reaction can be conducted at temperatures from 0° C. to the boiling point of the solvent selected but temperatures of about 70° C. are preferred.

Starting materials for preparing compounds of formula I can be prepared as described in Schemes II and III, below.

Scheme II

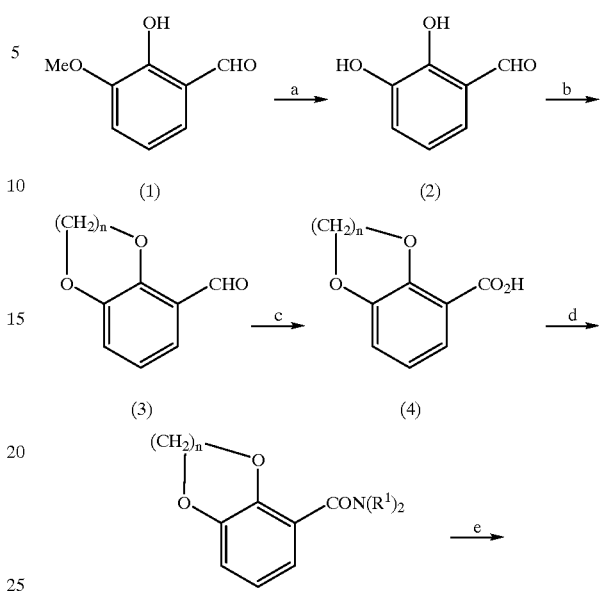

$R^1$ is lower alkyl

PG is a nitrogen protecting group

In step (a) commercially available starting material (1) is O-demethylated by refluxing in an acid, preferably acetic acid, along with hydrobromic acid for from 1 to 24 hours to prepare (2).

Under an inert atmosphere, such as nitrogen, intermediate (2) is dissolved in an aprotic polar solvent such as dimethylformamide. A base such as cesium carbonate is added and the solution is treated with an alkyl-dihalide of the formula $X(CH_2)_nX$, where X is a halogen, preferably bromide, and the reaction is preferable heated to about 50° C. to 130° C., preferably at 110° C., for from 1 to 24 hours to form (3).

Heating the aldehyde (3) in step (c) with an excess of potassium permanganate in water, achieves the acid (4). Temperatures of from about 80° C. are preferred, but the reaction may be run at temperatures of from about 20° C. to 100° C.

Conversion of the acid (4) to the amide (5) can be accomplished by treatment first with an acid chloride, preferably oxalyl chloride, followed by treatment with an appropriately substituted amine of the formula $HNR^1R^2$ where $R^1$ and $R^2$ are lower alkyl, for example, diethylamine. The first step is preferably conducted at ambient temperatures in a non polar solvent such as benzene and is facilitated by the addition of dimethylformamide (DMF). The second step is conducted at temperatures of about 0° C. using an aprotic polar solvent such as tetrahydrofuran (THF) and an excess of amine.

Intermediate (6) is achieved in step (e). Amide (5) is dissolved in an aprotic polar solvent such as THF, preferably along with N,N,N',N'-tetramethylethylenediamine (TMEDA) as a cosolvent, at temperatures of about −78° C. The solution is then treated with a strong base such as sec-butyl lithium, tert-butyl lithium or n-butyl lithium and then with N-protected piperidone.

Reduction of (6) using, for example, an excess of borane or diborane in THF at temperatures of about 0° C., prepares (7).

N-deprotection of either (6) or (7) can be accomplished as shown in steps (g) and (h) by refluxing with an excess of 1-chloroethyl chloroformate in an alkyl halide solvent such as ethylene dichloride at ambient temperatures followed by reflux in a lower alcohol solvent such as methanol or ethanol.

Scheme III

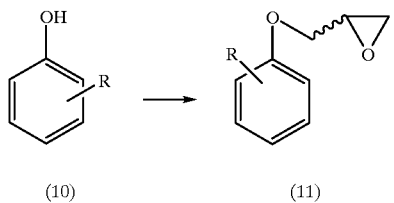

(10)          (11)

Under an inert atmosphere, such as nitrogen, an appropriately substituted phenol (10) is dissolved in an aprotic polar solvent such as DMF The solution is treated with sodium hydride then with S-glycidyl nosylate which has been chilled to temperatures of about 0° C.

The intermediates and final products may be isolated and purified by conventional techniques, for example silica gel chromatography then purification by conventional techniques such as chromatography or recrystallization.

It will be readily appreciated by the skilled artisan that the starting materials which are not described are either commercially available or can be readily prepared by known techniques from commercially available starting materials. All other reactants used to prepare the compounds in the instant invention are commercially available.

The following preparations and examples further illustrate the preparation of the compounds of this invention. The examples are illustrative only and are not intended to limit the scope of the invention in any way.

The first group of preparations (Preparations 1 to 4) illustrates typical synthesis of intermediates (8) and (9) used for preparing compounds of Formula I.

The second group of preparations (Preparation 5 and 6) illustrates synthesis of intermediate (11), also used for preparing compounds of Formula I.

Preparation 1

(4,5-Ethylenedioxy)spiro(isobenzofuran-1(3H),4'-piperidin)-3-one

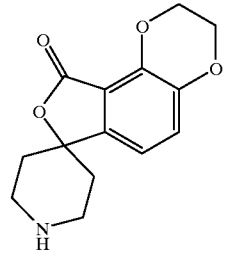

A. Preparation of 2,3-dihydroxybenzaldehyde

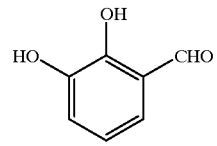

Into a 500 ml round bottom flask fitted with a nitrogen inlet, condenser, and a magnetic stirring bar were placed o-vanillin (50 g, 330 mmol), 200 ml glacial acetic acid, and 60 ml of 48% hydrobromic acid. The mixture was heated to reflux and allowed to stir for 18 hours. The solvent was distilled off and the residue was taken up in methanol and filtered. The filtrate was concentrated and the residue taken up in methylene chloride. This solution was washed three times with sodium bicarbonate, twice with brine, dried over sodium sulfate, filtered, and concentrated. The crude product was dissolved in 0–2% methanol in methylene chloride and chromatographed (100:10:1 methylene chloride:methanol:ammonium hydroxide) to give 12.49g. of subtitled product (27%) which was used directly in the next step.

B. Preparation of 2,3-ethylenedioxybenzaldehyde

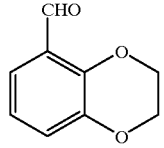

Into a 100 ml round bottom flask fitted with a nitrogen gas inlet, condenser, and a magnetic stirring bar were placed 2,3-dihydroxybenzaldehyde (4.00 g, 29.0 mmol), 70 ml anhydrous dimethylformamide, and cesium carbonate (14.15 g, 43.5 mmol). The mixture was heated to 110° and stirred for 2.5 hours. The reaction was allowed to cool to room temperature and ethyl acetate was added. This solution was washed four times with brine, dried over sodium sulfate, filtered, and concentrated. The residue was chromatographed (0–10% ethyl acetate/hexanes to give 4.07 g of subtitled product (86%) which was used directly in the next step.

C. Preparation of 2,3-ethylenedioxybenzoic acid

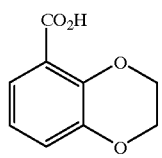

Into a 500 ml round bottom flask fitted with a 250 ml addition funnel and a magnetic stir bar were placed 2,3-ethylenedioxybenzaldehyde (4.07 g, 24.7 mmol) and 100 ml of water. The mixture was heated to 80° and potassium permanganate (7.84 g, 49.6 mmol) in 150 ml of water was added dropwise via the addition funnel over 20 minutes. After the addition was complete the mixture was allowed to stir at 80° for 1.5 hours. The mixture was made basic with a 10% potassium hydroxide solution and the solids filtered. The filter cake was washed with hot water. The filtrate was extracted with ether, made acidic, then extracted with ethyl acetate. The organics were dried over sodium sulfate, filtered, and concentrated to give 2.96 g of subtitled product (66%) which was used directly in the next step.

D. Preparation of (2,3-ethylenedioxy) diethylbenzamide

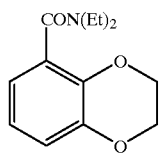

Into a 250 ml round bottom flask fitted with a nitrogen inlet and magnetic stirring bar were placed 32.8 ml of benzene and 2,3-ethylenedioxybenzoic acid (2.96 g, 16.4 mmol). The mixture was stirred into a suspension before adding oxalyl chloride (4.3 ml, 8.88 mmol) via a syringe. The mixture was cooled to 0° and 5 drops of dimethylformamide added. The mixture was allowed to warm to room temperature over 1 hour before concentrating the mixture in vacuo. The residue was taken up in 52.5 ml of anhydrous tetrahydrofuran and cooled to 0° before adding diethylamine (17 ml, 164 mmol) dropwise over 10 minutes. The mixture was then allowed to warm to room temperature and diluted with ethyl acetate. The mixture was washed twice with brine, dried over sodium sulfate, filtered, and concentrated to give 3.71 g of subtitled product (96%) which was used directly in the next step.

E. Preparation of 1'-methyl-(4,5-ethylenedioxy) spiro(isobenzofuran-1(3H),4'-piperidin)-3-one

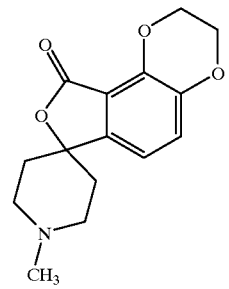

Into a 250 ml oven dried round bottom flask fitted with a nitrogen inlet and a magnetic stirring bar were placed (2,3-ethyldioxy)diethylbenzamide (3.71 g, 15.8 mmol), 79 ml of anhydrous tetrahydrofuran, and N,N,N',N'-tetramethylethylenediamine (2.4 ml, 15.8 mmol). The mixture was cooled to −78° and sec butyl lithium added (1.3 M in cylcohexane, 18.2 ml, 23.7 mmol). After the addition was complete, the mixture was allowed to stir at −78° for 1.5 hours. N-methylpiperidone (1.79 g, 15.8 mmol) in 32 ml of anhydrous tetrahydrofuran was then slowly added via syringe before allowing the mixture to warm to room temperature. The reaction was quenched with 16 ml of 5N hydrochloric acid. The layers were separated and the organics were extracted with 1N hydrochloric acid. The aqueous extracts were combined and made basic with concentrated ammonium hydroxide. Sodium chloride was then added past the point of saturation and the mixture was extracted with ethyl acetate. The organics were dried over sodium sulfate, filtered, and concentrated. The crude product residue was taken up in 2% methanol:methylene chloride and chromatographed (100:10:1 methylene chloride:methanol:ammonium hydroxide) to give 1.63 g of subtitled product (38%) which was used directly in the next step.

F. Preparation of (4,5-ethylenedioxy)spiro (isobenzofuran-1(3H),4'-piperidin)-3-one

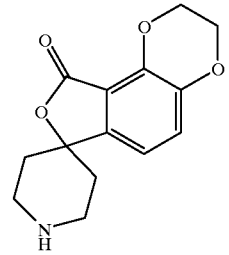

Into a 25 ml round bottom flask fitted with a nitrogen inlet, condenser, and a magnetic stirring bar were placed 1'-methyl-(4,5-ethylenedioxy)spiro(isobenzofuran-1(3H), 4'-piperidin)-3-one (501 mg, 1.82 mmol) and 5.5 ml of 1,2-dichloroethane. The mixture was cooled to 0° before 1-chloroethyl chloroformate (0.8 ml, 7.28 mmol) was added slowly via a syringe. The mixture was then heated to reflux for 72 hours. The mixture was concentrated in vacuo and the residue taken up in 5.5 ml of methanol. This mixture was heated to reflux for 3 hours before concentration. This residue was diluted with water and made basic with concentrated ammonium hydroxide. The aqueous mixture was extracted with ethyl acetate. The organics were washed with brine, dried over sodium sulfate, filtered, and concentrated. The residue was taken up in 2% methanol:ammonium hydroxide and chromatographed (100:10:1 methylene chloride:methanol:ammonium hydroxide) to give 203 mg of title product (43%).

Preparation 2

(4,5-Ethylenedioxy)spiro(isobenzofuran-1(3H),4'-piperidine)

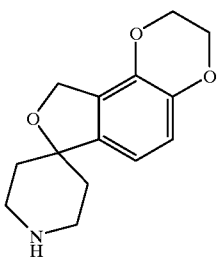

A. Preparation of 1'-methyl-(4,5-ethylenedioxy)spiro(isobenzofuran-1(3H),4'-piperidine)

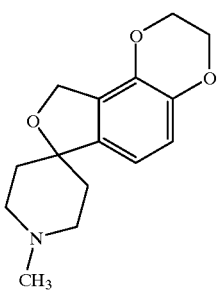

Into a 100 ml round bottom flask fitted with a nitrogen inlet, condenser, and magnetic stirring bar containing 10.9 ml of anhydrous tetrahydrofuran at 0° was placed 1'-methyl-(4,5-ethylendioxy)spiro(isobenzofuran-1(3H),4'-piperidin)-3-one (1.124 g, 4.08 mmol). Borane tetrahydrofuran complex (1.0 M in tetrahydrofuran, 10.2 mmol) was added slowly via syringe. The mixture was heated to reflux for 72 hours and then cooled to 0°. 5N hydrochloric acid (4 ml) was then added via syringe before heating the mixture to reflux again for 5 hours. The solution was then concentrated in vacuo and partitioned between ethyl acetate and water. The aqueous layer was made basic with concentrated ammonium hydroxide and sodium chloride was added past point of saturation. The aqueous layer was extracted again with ethyl acetate (three times) and the combined organics were dried over sodium sulfate, filtered, and concentrated. The residue was taken up in 2% methanol:ammonium hydroxide and chromatographed (100:10:1 methylene chloride:methanol:ammonium hydroxide) to give 750 mg of subtitled product (70%) which was used directly in the next step.

B. Preparation of (4,5-ethylenedioxy)spiro(isobenzofuran-1(3H),4'-piperidine)

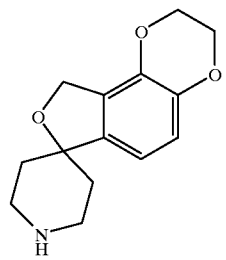

1'-methyl(4,5-ethylenedioxy)spiro(isobenzofuran-1(3H),4'-piperidine) (750 mg, 2.87 mmol) was converted, by the procedure of Preparation 1, step F, to give 295 mg of the title compound (42%).

Preparation 3

(4,5-Propylenedioxy)spiro(isobenzofuran-1(3H),4'-piperidin)-3-one

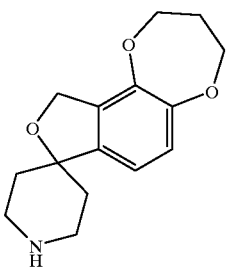

A. Preparation of (2,3-propyeneldioxy)benzaldehyde

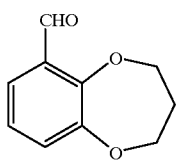

2,3-dihydroxybenzaldehyde (4.00 g, 29.0 mmol) was converted by the procedure of Preparation 1, step B, to 3.59 g of subtitled product (70%).

B. Preparation of (2,3-propylenedioxy)benzoic acid

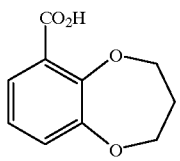

(2,3-propylenedioxy)benzaldehyde(3.59 g, 20.1 mmol) was converted by the procedure of Preparation 1, step C, to 3.29 g of product (84%).

C. Preparation of (2,3-propylenedioxy)diethylbenzamide

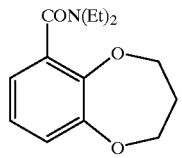

(2,3-propylenedioxy)benzoic acid (3.29 g, 16.9 mmol) was converted, by the procedure of Preparation 1, step D, to 4.11 g of subtitled product (97%).

D. Preparation of 1'-methyl-(4,5-propylenedioxy)spiro(isobenzofuran-1(3H),4'-piperidin)-3-one

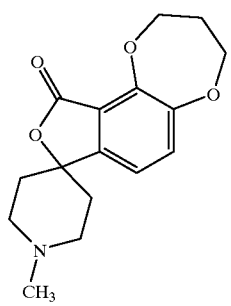

(2,3-propylenedioxy)diethylbenzamide (4.11 g, 16.5 mmol) was converted, by the procedure of Preparation 1, step E, to 3.05 g of subtitled product (64%).

E. Preparation of (4,5-propylenedioxy)spiro(isobenzofuran-1(3H),4'-piperidin)-3-one

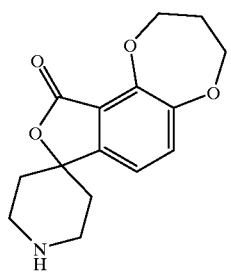

1'-methyl-(4,5-propylenedioxy)spiro(isobenzofuran-1(3H),4'-piperidin)-3-one (606 mg, 2.09 mmol) was converted, by the procedure of Preparation 1, step F, to 474 mg of title product (82%).

Preparation 4

(4,5-Propylenedioxy)spiro(isobenzofuran-1(3H),4'-piperidine)

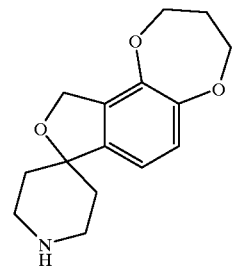

A. Preparation of 1'-methyl-(4,5-propylenedioxy)spiro(isobenzofuran-1(3H),4'-piperidine)

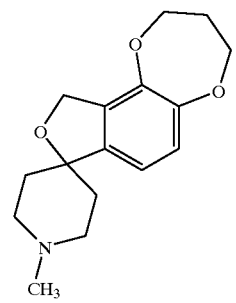

1'-methyl-(4,5-propylenedioxy)spiro(isobenzofuran-1(3H),4'-piperidin)-3-one (2.445 g, 8.45 mmol) was converted, by the procedure of Preparation 2, Step A, to 1.84 g of subtitled product (79%).

B. Preparation of (4,5-propylenedioxy)spiro(isobenzofuran-1(3H),4'-piperidine)

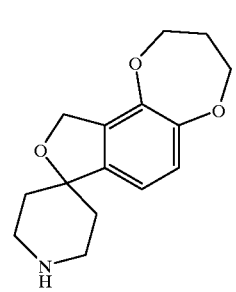

1-methyl-(4,5-propylenedioxy)spiro(isobenzofuran-1(3H),4'-piperidine (1.84 g, 6.68 mmol) was converted, by the procedure of Preparation 1, Step F, to 1.156 g of title product (66%).

Preparation 5

(S)-(+)-2-(oxiranylmethoxy)methylthiobenzene

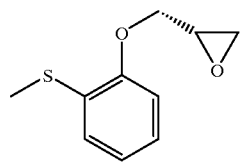

Into a 200 ml round bottom flask fitted with a nitrogen inlet and condenser containing 71 ml of anhydrous dimethylformamide was placed (2-hydroxy)thioanisole (5.00 g, 35.7 mmol). Sodium hydride (1.47 g, 60% in oil, 36.8 mmol) was then added in portions over 5 minutes. The resulting solution was allowed to stir at room temperature for 2 hours. The solution was cooled to 0° before s-glycidal-nosylate (9.24 g, 35.7 mmol), in 23 ml of anhydrous dimethylformamide, was added via an addition funnel over 10 minutes. After the addition was complete the solution was allowed to warm to room temperature before being diluted with ethyl acetate. This mixture was washed with water, brine, dried over sodium sulfate, filtered, then concentrated. The crude product was chromatographed 0–5% ethyl acetate/hexane to give 4.27 g of title product (61%).

Preparation 6

(S)-(+)-2-(oxiranylmethoxy)cyclopentylbenzene

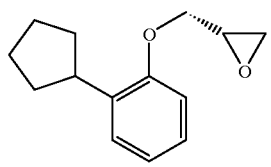

(2-Cyclopentyl)phenol (5.79 g, 35.7 mmol) and s-glycidal-nosylate (9.24 g, 35.7 mmol) were converted to product by the procedure of Preparation 5 to give 6.07 g of title product (78%).

mp 31° C.

EXAMPLE 1

(2S)-(−)-1-(2-methylthiophenoxy)-3-(4,5-ethylenedioxy)spiro(isobenzofuran-1(3H),4'-piperidin)1'-yl)-2-propanol ethanedioate

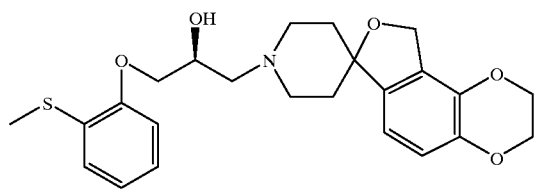

Into a 25 ml round bottom flask fitted with a nitrogen gas inlet, condenser, and magnetic stirring bar containing 3 ml of methanol was placed the compound of Preparation 2, (159 mg, 0.64 mmol) and the compound of Preparation 5 (126 mg, 0.64 mmol). The mixture was heated to 70° for 18 hours. The reaction was cooled to room temperature and concentrated in vacuo. The residue was taken up in 0–2% methanol/methylene chloride and chromatographed (100:10:1 methylene chloride:methanol:ammonium hydroxide to give 167 mg of the free base title product (59%). MS(FD) 443.2. This product was precipitated as its oxalate salt.

mp. 180–180° C.

Elemental Analysis calculated: $C_{26}H_{31}NO_9S$ Theoretical: C, 58.53; H, 5.86; N, 2.63 Found: C, 58.24; H, 5.68; N, 2.63

EXAMPLE 2

(2S)-(−)-1-(2-thiomethylphenoxy)-3-(4,5-ethylenedioxy)spiro(isobenzofuran-1(3H),4'-piperidin)-3-one-1'-yl)-2-propanol ethanedioate

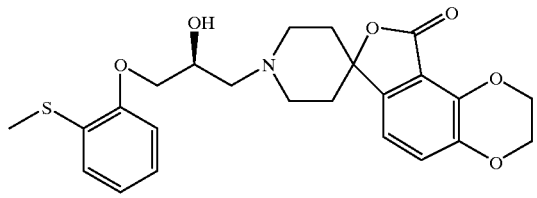

The compound of Preparation 1 (64 mg, 0.24 mmol) and the compound of Preparation 5 (48 mg, 0.24 mmol) were converted to title product free base by the procedure of Example 1 to give 45 mg (40%). Free base was precipitated as an oxalate salt.

MS(FD) 458.

Elemental Analysis calculated: $C_{26}H_{29}NO_{10}S$ Theoretical: C, 57.03; H, 5.34; N, 2.56 Found: C, 57.02; H, 5.43; N, 2.70.

EXAMPLE 3

(2S)-(−)-1-(2-methylthiophenoxy)-3-(4,5-propylenedioxy)spiro(isobenzofuran-1(3H),4'-piperidin)-1'-yl)-2-propanol

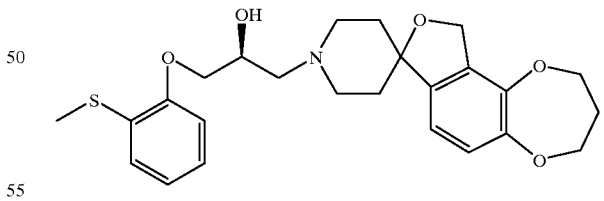

The compound of Preparation 4 (584 mg, 2.23 mmol) and the compound of Preparation 5 (439 mg, 2.23 mmol) were converted to title product by the procedure of Example 1 to give 757 mg (74%).

MS(FD) 457.1

Elemental Analysis calculated: $C_{25}H_{31}NO_5S$ Theoretical: C, 65.62; H, 6.83; N, 3.06. Found: C, 65.90; H, 6.87; N, 3.14.

EXAMPLE 4

(2S)-(−)-1-(2-methylthiophenoxy)-3-(4,5-propylenedioxy)spiro(isobenzofuran-1(3H),4'-piperidin)-3-one-1'-yl)-2-propanol

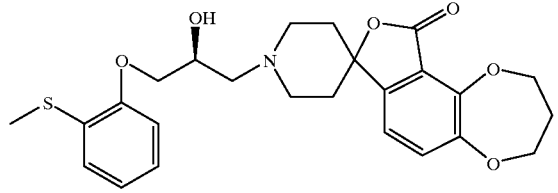

The compound of Preparation 3 (100 mg, 0.36 mmol) and the compound of Preparation 5 (71 mg, 0.36 mmol) were converted to title product by the procedure of Example 1 to give 62 mg. (36%).

MS(FD) 471.0,

Elemental Analysis calculated: $C_{25}H_{29}NO_6S$ Theoretical: C, 63.67; H, 6.20; N, 2.97. Found: C, 63.80; H, 6.13; N, 2.97.

EXAMPLE 5

(2S)-(−)-1-(2-cyclopentylphenoxy)-3-(4,5-ethylenedioxy)spiro(isobenzofuran-1(3H),4'-piperidin)-1'-yl)-2-propanol ethanedioate

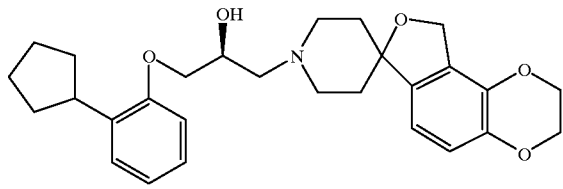

The compound of Preparation 2 (136 mg, 0.55 mmol) and the compound of Preparation 6 (120 mg, 0.55 mmol) were converted to title product by the procedure of Example 1 to give 157 mg. (61%).

mp 198–200° C. (oxalate salt)

MS(FD) 465.2,

Elemental Analysis calculated: $C_{28}H_{35}NO_5$ Theoretical: C, 72.23; H, 7.58; N, 3.01. Found: C, 72.44; H, 7.42; N, 3.17.

EXAMPLE 6

(2S)-(−)-1-(2-cyclopentylphenoxy)-3-(4,5-ethylenedioxy)spiro(isobenzofuran-1(3H),4'-piperidin)-3-one-1'-yl)-2-propanol ethanedioate

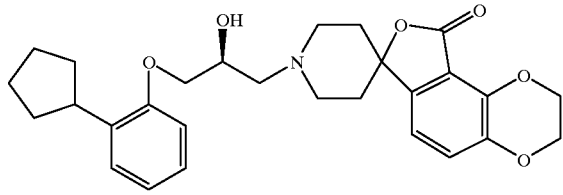

The compound of Preparation 1 (64 mg, 0.24 mmol) and the compound of Preparation 6 (53 mg, 0.24 mmol) were converted to title product by the procedure of Example 1 to give 67 mg of the oxalate salt. (57%).

MS(FD) 480.

Elemental Analysis calculated: $C_{30}H_{35}NO_{10}$ Theoretical: C, 63.26; H, 6.18; N, 2.46 Found: C, 63.03; H, 6.21; N, 3.56

EXAMPLE 7

(2S)-(−)-1-(2-cyclopentylphenoxy)-3-(4,5-propylenedioxy)spiro(isobenzofuran-1(3H),4'-piperidin)-1'-yl)-2-propanol ethanedioate

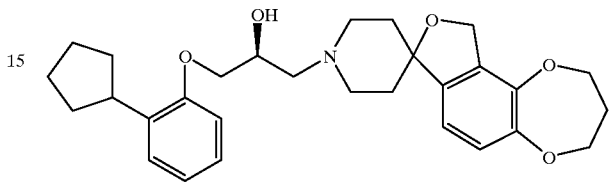

The compound of Preparation 4 (572 mg, 2.19 mmol) and the compound of Preparation 6 (478 mg, 2.19 mmol) were converted to title product by the procedure of Example 1 to give 814 mg of the oxalate salt. (78%).

MS(FD) 479.1.

mp 169–171° C.

Elemental Analysis calculated: $C_{31}H_{39}NO_9$ Theoretical: C, 72.62; H, 7.78; N, 2.92 Found: C, 72.46; H, 7.83; N, 3.13

EXAMPLE 8

(2S)-(−)-1-(2-cyclopentylphenoxy)-3-(4,5-propylenedioxy)spiro(isobenzofuran-1(3H),4'-piperidin)-3-one-1'-yl)-2-propanol ethanedioate

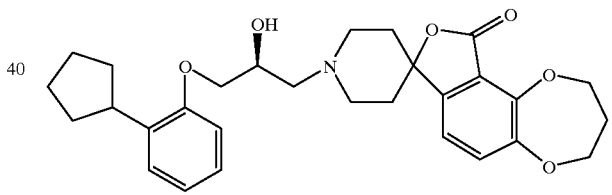

The compound of Preparation 3 (100 mg, 0.36 mmol) and the compound of Preparation 6 (79 mg, 0.364 mmol) were converted to title product by the procedure of Example 1 to give 96 mg of the oxalate salt. (54%).

MS(FD) 493.1.

Elemental Analysis calculated: $C_{31}H_{37}NO_{10}$ Theoretical: C, 70.57; H, 7.15; N, 2.84 Found: C, 70.53; H, 6.87; N, 2.86

The method of this invention is practiced by administering to a mammal a direct acting $5\text{-HT}_{1A}$ and $5\text{-HT}_{1D\alpha}$ antagonist or a pharmaceutically acceptable salt thereof. The phrase "direct acting $5\text{-HT}_{1A}$ and $5\text{-HT}_{1D\alpha}$ antagonist" as used in this specification and these claims means a non-endogenous chemical compound and includes: (1) synthetic chemical compounds (ligands) that block the action of serotonin on $5\text{-HT}_{1A}$ and $5\text{-HT}_{1D\alpha}$ receptors by directly inhibiting these receptors; and (2) partial agonists, which are synthetic chemical compounds (ligands) that block the action of serotonin on $5\text{-HT}_{1A}$ and $5\text{-HT}_{1D\alpha}$ receptors by directly inhibiting these receptors but produce a smaller maximal effect than do other ligands that act on the same receptor. These compounds may have activity at other receptors but must have some component of 5-HT$_{1A}$ and 5-HT$_{1D\alpha}$ antagonist activity.

Assay Experiments
Serotonin $1_A$ Receptor Activity

The compounds of the present invention are active at the serotonin $1_A$ receptor, particularly as antagonists and as partial agonists at that receptor.

The 5HT-$1_A$ receptor binding potency of the present compounds has been measured by a modification of the binding assay described by Taylor, et al. (*J. Pharmacol. Exp. Ther.*, 236, 118–125, 1986); and Wong, et al., *Pharm. Biochem. Behav,.* 46, 173–77 (1993). Membranes for the binding assay were prepared from male Sprague-Dawley rats (150–250 g). The animals were killed by decapitation, and the brains were rapidly chilled and dissected to obtain the hippocampi. Membranes from the hippocampi were either prepared that day, or the hippocampi were stored frozen (−70°) until the day of preparation. The membranes were prepared by homogenizing the tissue in 40 volumes of ice-cold Tris-HCl buffer (50 mM, pH 7.4 at 22°) using a homogenizer for 15 sec., and the homogenate was centrifuged at 39800×g for 10 min. The resulting pellet was then resuspended in the same buffer, and the centrifugation and resuspension process was repeated three additional times to wash the membranes. Between the second and third washes the resuspended membranes were incubated for 10 minutes at 37° to facilitate the removal of endogenous ligands. The final pellet was resuspended in 67 mM Tris-HCl, pH 7.4, to a concentration of 2 mg of tissue original wet weight/200 $\mu$l. This homogenate was stored frozen (−70°) until the day of the binding assay. Each tube for the binding assay had a final volume of 800 $\mu$l and contained the following: Tris-HCl (50 mM), pargyline (10 $\mu$M), CaCl$_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes were incubated for either 10 minutes filtered through GF/B filters (pretreated with 0.5% polyethylenimine), followed by four one-ml washes with ice-cold buffer. The radioactivity trapped by the filters was quantitated by liquid scintillation spectrometry, and specific [$^3$H]8-OH-DPAT binding to the 5-HT$_{1A}$ sites was defined as the difference between [$^3$H]8-OH-DPAT bound in the presence and absence of 10 $\mu$M 5-HT.

IC$_{50}$ values, i.e., the concentration required to inhibit 50% of the binding, were determined from 12-point competition curves using nonlinear regression (SYSTAT, SYSTAT, Inc., Evanston, Ill.).

Additional binding assays of some of the present compounds have been carried out by an assay method which uses a cloned cell line which expresses the serotonin 1A receptor, rather than the hippocampal membranes. Such cloned cell lines have been described by Fargin, et al., *J. Bio. Chem.*, 264, 14848–14852 (1989), Aune, et al., *J. Immunology*, 151, 1175–1183 (1993), and Raymond, et al., *Naunyn-Schmiedeberg's Arch. Pharmacol.*, 346, 127–137 (1992). Results from the cell line assay are substantially in agreement with results from the hippocampal membrane assay.
Serotonin $1_{D\alpha}$ Receptor Activity The ability of the compounds of this invention to bind to the 5-HT$_{1D\alpha}$ receptor subtype was measured essentially as described in N. Adham, et al., *Proceedings of the National Academy of Sciences (USA)*, 90, 408–412 (1993).

Membrane Preparation: Membranes were prepared from transfected Ltk-cells which were grown to 100% confluency. The cells were washed twice with phosphate-buffered saline, scraped from the culture dishes into 5 ml of ice-cold phosphate-buffered saline, and centrifuged at 200×g for 5 minutes at 4° C. The pellet was resuspended in 2.5 mL of ice-cold Tris buffer (20 mM Tris HCl, pH=7.4 at 23° C., 5 mM EDTA) and homogenized with a Wheaton tissue grinder. The lysate was subsequently centrifuged at 200×g for 5 minutes at 4° C. to pellet large fragments which were discarded. The supernatant was collected and centrifuged at 40,000×g for 20 minutes at 4° C. The pellet resulting from this centrifugation was washed once in ice-cold Tris wash buffer and resuspended in a final buffer containing 50 mM Tris HCl and 0.5 mM EDTA, pH=7.4 at 23° C. Membrane preparations were kept on ice and utilized within two hours for the radioligand binding assays. Protein concentrations were determined by the method of Bradford (*Anal. Biochem.*, 72, 248–254 (1976)).

Radioligand Binding: [$^3$H-5-HT] binding was performed using slight modifications of the 5-HT$_{1D}$ assay conditions reported by Herrick-Davis and Titeler (*J. Neurochem.*, 50, 1624–1631 (1988)) with the omission of masking ligands. Radioligand binding studies were achieved at 37° C. in a total volume of 250 mL of buffer (50 mM Tris, 10 mM MgCl$_2$, 0.2 mM EDTA, 10 mM pargyline, 0.1% ascorbate, pH=7.4 at 37° C.) in 96 well microtiter plates. Saturation studies were conducted using [$^3$H]5-HT at 12 different concentrations ranging from 0.5 nM to 100 nM. Displacement studies were performed using 4.5–5.5 nM [$^3$H]5-HT. The binding profile of drugs in competition experiments was accomplished using 10–12 concentrations of compound. Incubation times were 30 minutes for both saturation and displacement studies based upon initial investigations which determined equilibrium binding conditions. Nonspecific binding was defined in the presence of 10 mM 5-HT. Binding was initiated by the addition of 50 mL membrane homogenates (10–20 $\mu$g). The reaction was terminated by rapid filtration through presoaked (0.5% poylethyleneimine) filters using 48R Cell Brandel Harvester (Gaithersburg, Md.). Subsequently, filters were washed for 5 seconds with ice cold buffer (50 mM Tris HCl, pH=7.4 at 4° C.), dried and placed into vials containing 2.5 mL Readi-Safe (Beckman, Fullerton, Calif.) and radioactivity was measured using a Beckman LS 5000TA liquid scintillation counter. The efficiency of counting of [$^3$H]5-HT averaged between 45–50%. Binding data was analyzed by computer-assisted nonlinear regression analysis (Accufit and Accucomp, Lunden Software, Chagrin Falls, Ohio). ICS0 values were converted to $K_i$ values using the Cheng-Prusoff equation (*Biochem. Pharmacol.*, 22, 3099–3108 (1973). All experiments were performed in triplicate.

Representative compounds of the invention exhibited an Ki at the 5-HT$_{1A}$ and 5-HT$_{1D\alpha}$ receptors of at least 300 $\mu$mol.

As was reported by R. L. Weinshank, et al., WO93/14201, the 5-HT$_{1A}$ and 5-HT$_{1D}$ receptors are functionally coupled to a G-protein as measured by the ability of serotonin and serotonergic drugs to inhibit forskolin stimulated cAMP production in NIH3T3 cells transfected with the 5-HT$_{1A}$ or 5-HT$_{1D}$ receptors. Adenylate cyclase activity was determined using standard techniques. A maximal effect is achieved by serotonin. An E$_{max}$ is determined by dividing the inhibition of a test compound by the maximal effect and determining a percent inhibition. (N. Adham, et al., supra,; R. L. Weinshank, et al., *Proceedings of the National Academy of Sciences (USA)*, 89,3630–3634 (1992)), and the references cited therein.
Measurement of cAMP Formation Transfected NIH3T3 cells (estimated Bmax from one point competition studies=488 fmol/mg of protein) were incubated in DMEM, 5 mM theophylline, 10 mM HEPES (4-[2-hydroxyethyl]-1-piperazineethanesulfonic acid) and 10 µM pargyline for 20 minutes at 37° C., 5% $CO_2$. Drug dose-effect curves were then conducted by adding 6 different final concentrations of drug, followed immediately by the addition of forskolin (10 mM). Subsequently, the cells were incubated for an additional 10 minutes at 37° C., 5% $CO_2$. The medium was aspirated and the reaction was stopped by the addition of 100 mM HCl. To demonstrate competitive antagonism, a dose-response curve for 5-HT was measured in parallel, using a fixed dose of methiothepin (0.32 mM). The plates were stored at 4° C. for 15 minutes and then centrifuged for 5 minutes at 500×g to pellet cellular debris, and the supernatant was aliquoted and stored at −20° C. before assessment of cAMP formation by radioimmunoassay (cAMP radioimmunoassay kit; Advanced Magnetics, Cambridge, Mass.). Radioactivity was quantified using a Packard COBRA Auto Gamma counter, equipped with data reduction software. Representative compounds were tested and found to be antagonists at the $5\text{-}HT_{1A}$ and $5\text{-}HT_{1D\alpha}$ receptors in the cAMP assay.

Pharmaceutical Formulations of the Invention

Throughout this document, the person or animal to be treated will be described as a "mammal", and it will be understood that the most preferred subject is a human. However it must be noted that the study of adverse conditions of the central nervous system in non-human animals is only now beginning, an that some instances of such treatments are coming into use. Accordingly, use of the present compounds in non-human animals is contemplated. It will be understood that the dosage ranges for other animals will necessarily be quite different from the doses administered to humans, and accordingly that the dosage ranges described be recalculated. For example, a small dog may be only $\frac{1}{10}^{th}$ of a typical human's size, and it will therefore be necessary for a much smaller dose to be used. The determination of an effective amount for a certain non-human animal is carried out in the same manner described below in the case of humans, and veterinarians are well accustomed to such determinations.

The activity of the compounds at the serotonin $1_A$ and $1_{D\alpha}$ receptor provides a method of affecting the serotonin $1_A$ and $1_{D\alpha}$ receptor which comprises administering to a subject in need of such treatment and effective amount of a compound of Formula I. Reasons for the necessity of affecting the $1_A$ and $1_{D\alpha}$ receptor will be described in detail below, but in all cases the effect on the serotonin $1_A$ and $1_{D\alpha}$ receptor is brought about through the compounds' potency as antagonists or partial agonists at that receptor. A mammal in need of a modification of the effects of the $5\text{-}HT_{1A}$, $5\text{-}HT_{1D\alpha}$ or $5\text{-}HT_{1A}$ and $5\text{-}HT_{1D\alpha}$ receptors is one having one or more of the specific conditions and problems to be further described, or a condition or problem not yet recognized as created by an imbalance or malfunction of the $5\text{-}HT_{1A}$ or $5\text{-}HT_{1D}$ receptor, since research on the central nervous system is presently ongoing in many fields and newly discovered relationships between receptors and therapeutic needs are continually being discovered. In all cases, however, it is the compounds' ability to affect the serotonin $1_A$ or $1_{D\alpha}$ receptor which creates their physiological or therapeutic effects.

The therapeutic and prophylactic treatments provided by this invention are practiced by administering to a mammal in need thereof a dose of a compound of formula I, or a pharmaceutically acceptable salt thereof, that is effective in inhibiting the $5\text{-}HT_{1A}$ and $5\text{-}HT_{1D\alpha}$ receptor.

While it is possible to administer a compound employed in the methods of this invention directly without any formulation, the compounds are usually administered in the form of pharmaceutical formulation comprising a pharmaceutically acceptable excipient and at least one compound of the present invention. The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 0.01 to 90% by weight of the active compound in a suitable base, soft and hard gelatin capsules, suppositories, injectable solutions and suspensions in physiologically acceptable media, and sterile packaged powders adsorbed onto a support material for making injectable solutions. Such formulations are prepared in a manner well known in the pharmaceutical art and comprise at least one active compound. See. e.g., Remington's Pharmaceutical Sciences, (16th ed. 1980).

In making the formulations employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For topical administration, a compound of this invention ideally can be admixed with any variety of excipients in order to form a viscous liquid or cream-like preparation.

For oral administration, a compound of this invention ideally can be admixed with carriers and diluents and molded into tablets or enclosed in gelatin capsules.

In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention include capsules, tablets and injectable solutions. Especially preferred are capsules and tablets.

The therapeutic and prophylactic treatments provided by this invention are practiced by administering to a mammal in need thereof a dose of a compound of formula I or a pharmaceutically acceptable salt or solvate thereof that is effective to alleviate the pathological effects of $5\text{-HT}_{1A}$ and $5\text{-HT}_{1D\alpha}$ receptor-activated diseases.

Advantageously for this purpose, formulations may be provided in unit dosage form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The specific dose of a compound administered according to this invention to obtain therapeutic or prophylactic effects will, of course, be determined by the particular circumstances surrounding the case, including, for example, the route of administration the age, weight and response of the individual patient, the condition being treated and the severity of the patient's symptoms.

In general, the compounds of the invention are most desirably administered at a concentration that will generally afford effective results without causing any serious side effects and can be administered either as a single unit dose, or if desired, the dosage may be divided into convenient subunits administered at suitable times throughout the day.

Therapeutic Applications

The compounds of Formula I are valuable for binding, blocking or modulating the serotonin $1_A$ receptor, and for the treatment or prophylaxis of conditions caused by or influenced by defective function of that receptor. In particular, the compounds are useful for antagonism at the serotonin $1_A$ receptor and accordingly are used for the treatment or prevention of conditions caused by or affected by excessive activity of that receptor.

More particularly, the compounds are useful in the treatment of anxiety, depression, hypertension, cognitive disorders, psychosis, sleep disorders, gastric motility disorders, sexual dysfunction, brain trauma, memory loss, appetite disorders and obesity, substance abuse, obsessive-compulsive disease, panic disorder and migraine.

Anxiety and its frequent concomitant, panic disorder, may be particularly mentioned in connection with the present compounds. The subject is carefully explained by Diagnostic and Statistical Manual of Mental Disorders, published by the American Psychiatric Association, which classifies anxiety under its category 300.02.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293, 81, 293.82, 293.83, 310.10, 318.00, 317.00 migraine pain, particularly neuropathic pain bulimia, ICD 307.51, DSM 307.51 premenstrual syndrome or late luteal phase syndrome, DSM 307.90 alcoholism, ICD 305.0, DSM 305.00 and 303.90 tobacco abuse, ICD 305.1, DSM 305.10 and 292.00 panic disorder, ICD 300.01, DSM 300.01 and 300.21 anxiety, ICD 300.02, DSM 300.00 post-traumatic syndrome, DSM 309.89 memory loss, DSM 294.00 dementia of aging, ICD 290 social phobia, ICD 300.23, DSM 300.23 attention deficit hyperactivity disorder, ICD 314.0 disruptive behavior disorders, ICD 312 impulse control disorders, ICD 312, DSM 312.39 and 312.34 borderline personality disorder, ICD 301.82, DSM 301.83 chronic fatigue syndrome premature ejaculation, DSM 302.75 erectile difficulty, DSM 302.72 anorexia nervosa, ICD 307.1, DSM 307.10 disorders of sleep, ICD 307.4 autism mutism trichotillomania

It is well known that the chronic administration of nicotine results in tolerance and, eventually, dependence. The use of tobacco has become extremely widespread in all countries, despite the well known adverse efforts of the use of tobacco in all its forms. Thus, it is clear that tobacco use is extremely habit-forming, if not addictive, and that its use provides sensations to the user which are pleasant and welcome, even though the user may be fully aware of the drastic long term ill effects of its use.

Rather recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

Thus, the present method of preventing or alleviating the symptoms caused by withdrawal or partial withdrawal from the use of tobacco or of nicotine comprises the previously discussed method of affecting the serotonin $1_A$ receptor, in that the treatment method comprises the administration of an effective amount of one of the serotonin $1_A$ receptor-active compounds of Formula I to the subject. The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced, or partially replaced, their use of tobacco with the use of nicotine replacement therapy. Thus, such subjects can be assisted to reduce and even eliminate entirely their dependence on nicotine in all forms.

A particular benefit of therapy with the present compounds is the elimination or reduction of the weight gain which very often results from reducing or withdrawing from use of tobacco or nicotine.

It will be understood that the present invention is useful for preventing or alleviating the withdrawal symptoms which afflict subjects who are trying to eliminate or reduce their use of tobacco or nicotine. The common withdrawal symptoms of such people include, at least, irritability, anxiety, restlessness, lack of concentration, insomnia, nervous tremor, increased hunger and weight gain, lightheadedness, and the craving for tobacco or nicotine. The prevention or alleviation of such symptoms, when they are caused by or occur in conjunction with ceasing or reducing the subject's use of tobacco or nicotine is a desired result of the present invention and an important aspect of it.

The invention is carried out by administering an effective amount of a compound of Formula I to a subject who is in need of or carrying out a reduction or cessation of tobacco or nicotine use.

Preferred pathological conditions to be treated by inhibiting the $1_{D\alpha}$ receptor include depression, dementia, Parkinson's disease, anxiety, appetite modulation, sexual dysfunction, seasonal affective disorder, hyperprolactinemia, cerebral vascular disease, antisocial behavior, obsessive/compulsive disorder, amnesia, tardive dyskensia, hypertension and gastric motility disorder.

The following formulation examples may employ as active compounds any of the compounds of this invention. The examples are illustrative only and are not intended to limit the scope of the invention in any way.

Formulation 1

Hard gelatin capsules are prepared using the following ingredients:

| | Quantity (mg/capsule) |
|---|---|
| 2S)-(-)-1-(2-pentylthiophenoxy)-3-(4,5-ethylenedioxy)spiro(isobenzofuran-1(3H),4'-piperidin)1'-yl)-2-propanol maleate | 250 |
| Starch, dried | 200 |
| Magnesium stearate | 10 |
| Total | 460 mg |

Formulation 2

A tablet is prepared using the ingredients below:

| | Quantity (mg/tablet) |
|---|---|
| 2S)-(-)-1-(2-ethylthiophenoxy)-3-(4,5-ethylenedioxy)spiro(isobenzofuran-1(3H),4'-piperidin)1'-yl)-2-propanol hydrochloride | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg

Formulation 3

An aerosol solution is prepared containing the following components:

| | Weight |
|---|---|
| 2S)-(-)-1-(2-propylthiophenoxy)-3-(4,5-methylenedioxy)spiro(isobenzofuran-1(3H),4'-piperidin)1'-yl)-2-propanol | 0.25 |
| Ethanol | 25.75 |
| Propellant 22 | 74.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| 2S)-(-)-1-(2-cyclohexylphenoxy)-3-(4,5-propylenedioxy)spiro(isobenzofuran-1(3H),4'-piperidin)-3-one-1'-yl)-2-propanol | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| 2S)-(-)-1-(2-cyclopropylphenoxy)-3-(4,5-ethylenedioxy)spiro(isobenzofuran-1(3H),4'-piperidin)-3-one-1'-yl)-2-propanol maleate | 80 mg |
| Starch | 59 mg |
| Microcrystalline cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| | |
|---|---|
| 2S)-(-)-1-(2-cyclononylphenoxy)-3-(4,5-methylenedioxy)spiro(isobenzofuran-1(3H),4'-piperidin)1'-yl)-2-propanol ethanedioate | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| 2S)-(-)-1-(2-octylthiophenoxy)-3-(4,5-propylenedioxy)spiro(isobenzofuran-1(3H),4'-piperidin)-3-one-1'-yl)-2-propanol ethanedioate | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

We claim:

1. A compound of the formula (I)

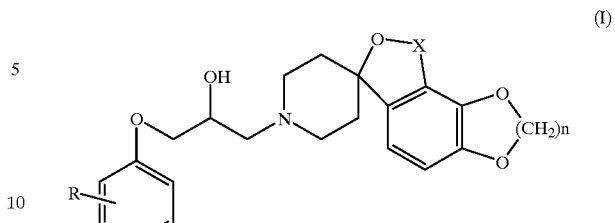

(I)

wherein:

R is —$(C_3$–$C_{10})$cycloalkyl or —$S(C_1$–$C_{10})$alkyl;

X is

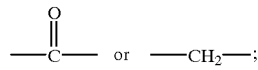

and n is an integer from 3 both inclusive;

or a pharmaceutically acceptable salt, racemate, optical isomer or solvate thereof.

2. A compound as claimed in claim 1 wherein R is —$(C_4$–$C_6)$cycloalkyl or —$S(C_1$–$C_4)$alkyl and n is 2 or 3.

3. A compound as claimed in claim 2 wherein R is cyclopentyl.

4. A compound as claimed in claim 2 selected from the group consisting of (2S)-(-)-1-(2-methylthiophenoxy)-3-(4,5-ethylenedioxy)spiro(isobenzofuran-1(3H),4'-piperidin)1'-yl)-2-propanol; (2S)-(-)-1-(2-methylthiophenoxy)-3-(4,5-ethylenedioxy)spiro(isobenzofuran-1(3H),4'-piperidin)-3-one-1'-yl)-2-propanol; (2S)-(-)-1-(2-cyclopentylphenoxy)-3-(4,5-ethylenedioxy)spiro(isobenzofuran-1(3H),4'-piperidin)-1'-yl)-2-propanol; (2S)-(-)-1-(2-cyclopentylphenoxy)-3-(4,5-ethylenedioxy)spiro(isobenzofuran-1(3H),4'-piperidin)-3-one-1'-yl)-2-propanol and (2S)-(-)-1-(2-cyclopentylphenoxy)-3-(4,5-propylenedioxy)spiro(isobenzofuran-1(3H),4'-piperidin)-3-one-1'-yl)-2-propanol or a pharmaceutically acceptable salt thereof.

5. The compound of claim 4 which is (2S)-(-)-1-(2-cyclopentylphenoxy)-3-(4,5-propylenedioxy)spiro(isobenzofuran-1(3H),4'-piperidin)-3-one-1'-yl)-2-propanol or a pharmaceutically acceptable salt thereof.

6. A pharmaceutical composition comprising a compound of formula I as claimed in claim 1 together with a pharmaceutically acceptable carrier or diluent therefor.

7. A method of inhibiting the 5-$HT_{1A}$ receptor which comprises administering to a mammal in need of such treatment a therapeutically effective amount of a direct acting 5-$HT_{1A}$ antagonist of formula I as claimed in claim 1.

8. A method of inhibiting the 5-$HT_{1D\alpha}$ receptor which comprises administering to a mammal in need of such treatment a therapeutically effective amount of a direct acting 5-$HT_{1D\alpha}$ antagonist of formula I as claimed in claim 1.

9. A method of inhibiting both the 5-$HT_{1A}$ and 5-$HT_{1D\alpha}$ receptors which comprises administering to a mammal in need of such treatment a therapeutically effective amount of a direct acting 5-$HT_{1D\alpha}$ antagonist of formula I as claimed in claim 1.

10. The method of claim 7 in which the compound is (2S)-(-)-1-(2-cyclopentylphenoxy)-3-(4,5-propylenedioxy)

spiro(isobenzofuran-1(3H),4'-piperidin)-3-one-1'-yl)-2-propanol or a pharmaceutically acceptable salt thereof.

11. The method of claim 8 in which the compound is (2S)-(−)-1-(2-cyclopentylphenoxy)-3-(4,5-propylenedioxy) spiro(isobenzofuran-1(3H),4'-piperidin)-3-one-1'-yl)-2-propanol or a pharmaceutically acceptable salt thereof.

12. The method of claim 9 in which the compound is (2S)-(−)-1-(2-cyclopentylphenoxy)-3-(4,5-propylenedioxy) spiro(isobenzofuran-1(3H),4'-piperidin)-3-one-1'-yl)-2-propanol or a pharmaceutucally acceptable salt thereof.

13. The method of claim 7 wherein the mammal is a human.

14. The method of claim 8 wherein the mammal is a human.

15. The method of claim 9 wherein the mammal is a human.

16. A method of alleviating the pathological effects of a disease mediated by inhibiting the 5-$HT_{1A}$ receptor in a mammal in need of such treatment comprising administering to said mammal a pharmaceutically effective amount of a direct acting 5-$HT_{1A}$ antagonist of formula I as claimed in claim 1.

17. A method of alleviating the pathological effects of a disease mediated by inhibiting the 5-$HT_{1D\alpha}$ receptor in a mammal in need of such treatment comprising administering to said mammal a pharmaceutically effective amount of a direct acting 5-$HT_{1D\alpha}$ antagonist of formula I as claimed in claim 1.

18. A method of alleviating the pathological effects of a disease mediated by the 5-$HT_{1A}$ and 5-$HT_{1D\alpha}$ receptors in a mammal in need of such treatment comprising administering to said mammal a pharmaceutically effective amount of a direct acting 5-$HT_{1A}$ antagonist of formula I as claimed in claim 1.

19. The method of claim 16 in which the receptor-activated diseases are withdrawal or partial withdrawal from the use of tobacco or of nicotine.

20. The method of claim 16 in which the disease is anxiety.

21. The method of claim 16 in which the disease is depression.

* * * * *